United States Patent
Bright (10) Patent No.: US 9,488,750 B2
(45) Date of Patent: Nov. 8, 2016

(54) WELLBORE FTIR GAS DETECTION SYSTEM

(71) Applicant: IBALL INSTRUMENTS LLC, Norman, OK (US)

(72) Inventor: Carl Bright, Harrah, OK (US)

(73) Assignee: IBALL INSTRUMENTS LLC, Norman, OK (US)

(*) Notice: Subject to any disclaimer, the term of this patent is extended or adjusted under 35 U.S.C. 154(b) by 0 days.

(21) Appl. No.: 14/954,170

(22) Filed: Nov. 30, 2015

(65) Prior Publication Data

US 2016/0084985 A1    Mar. 24, 2016

Related U.S. Application Data

(63) Continuation of application No. 14/327,263, filed on Jul. 9, 2014, now Pat. No. 9,217,810.

(60) Provisional application No. 62/001,298, filed on May 21, 2014.

(51) Int. Cl.
```
G01V 5/00      (2006.01)
G01V 8/02      (2006.01)
G01N 21/61     (2006.01)
G01N 21/3504   (2014.01)
G01N 21/35     (2014.01)
```

(52) U.S. Cl.
CPC ............. *G01V 8/02* (2013.01); *G01N 21/3504* (2013.01); *G01N 21/61* (2013.01); *G01N 2021/3595* (2013.01)

(58) Field of Classification Search
CPC .................. G01N 2021/3595; G01N 21/3504; G01N 21/61; G01V 8/02; G01V 5/04; G01V 5/045
USPC ........................................................ 250/255
See application file for complete search history.

(56) References Cited

U.S. PATENT DOCUMENTS

| | | | | |
|---|---|---|---|---|
| 3,215,900 A | * | 11/1965 | Harvey | G01N 27/223 137/93 |
| 4,635,735 A | * | 1/1987 | Crownover | E21B 49/08 175/42 |
| 5,138,163 A | * | 8/1992 | Butler | G01N 33/0011 250/339.08 |
| 6,039,783 A | * | 3/2000 | Lueck | B01D 53/56 422/170 |
| 6,058,773 A | * | 5/2000 | Zimmerman | E21B 49/082 73/152.24 |
| 6,263,724 B1 | * | 7/2001 | Devance | G01N 33/0006 73/1.06 |
| 7,595,876 B2 | * | 9/2009 | DiFoggio | G01J 3/02 250/269.1 |
| 8,445,841 B2 | * | 5/2013 | Szobota | G01N 21/3577 250/254 |
| 8,912,000 B2 | * | 12/2014 | Daniel | H01J 49/145 166/264 |
| 2003/0184733 A1 | * | 10/2003 | Kameoka | G01N 21/1702 356/73 |
| 2006/0093523 A1 | * | 5/2006 | Norman | G01N 33/2823 422/83 |
| 2006/0144126 A1 | * | 7/2006 | O'Brien | G01N 1/2202 73/23.42 |
| 2007/0266857 A1 | * | 11/2007 | Bentley | G01N 30/08 96/101 |
| 2009/0008560 A1 | * | 1/2009 | Gunn | G01N 21/3504 250/343 |
| 2010/0181471 A1 | * | 7/2010 | Pop | G01V 9/00 250/254 |

(Continued)

*Primary Examiner* — Mark R Gaworecki
*Assistant Examiner* — Taeho Jo
(74) *Attorney, Agent, or Firm* — Hall Estill Attorneys at Law; Tyler J. Mantooth (57) ABSTRACT

A system can be constructed and operated with at least a wellbore that is connected to a gas detection system. The gas detection system can house a control module, infrared sensor, and first and second pumps in a portable case. The first and second pumps may be respectively positioned on opposite sides of the infrared sensor and configured to provide uniform sample gas flow through the infrared sensor to detect multiple different types of gasses flowing from the wellbore.

20 Claims, 4 Drawing Sheets

(56) References Cited

U.S. PATENT DOCUMENTS

| | | | | |
|---|---|---|---|---|
| 2010/0300708 A1* | 12/2010 | Raphael | ............ | A61M 16/0477 169/54 |
| 2011/0139464 A1* | 6/2011 | Henderson | .............. | E21B 21/01 166/370 |
| 2011/0189778 A1* | 8/2011 | Daniel | .................. | H01J 49/145 436/25 |
| 2011/0231099 A1* | 9/2011 | Elkins | ...................... | B09B 1/00 702/12 |
| 2011/0270534 A1* | 11/2011 | Burba | ................ | G01N 21/3504 702/24 |
| 2013/0014943 A1* | 1/2013 | Harrison | ................ | G01N 21/66 166/264 |
| 2013/0019658 A1* | 1/2013 | Hao | .................. | B01D 46/2411 73/38 |
| 2013/0140453 A1* | 6/2013 | Verenchikov | .......... | H01J 49/107 250/282 |
| 2013/0224867 A1* | 8/2013 | Lorenz | .................. | G01N 17/00 436/2 |
| 2013/0263647 A1* | 10/2013 | Barrett | ............... | G01N 33/0016 73/31.07 |
| 2013/0270006 A1* | 10/2013 | Selman | ................... | E21B 49/08 175/24 |
| 2013/0273560 A1* | 10/2013 | Cooks | .................. | G01N 27/62 435/7.1 |
| 2013/0334412 A1* | 12/2013 | Gunn | ................ | G01N 33/2823 250/255 |
| 2014/0208826 A1* | 7/2014 | Larter | .................... | E21B 49/06 73/23.41 |
| 2014/0208840 A1* | 7/2014 | Bright | ............... | G01N 33/0006 73/152.19 |
| 2015/0107349 A1* | 4/2015 | Badri | ................... | E21B 49/005 73/152.04 |
| 2015/0136961 A1* | 5/2015 | Eddy | ................... | G01N 21/0332 250/255 |

* cited by examiner

WELLBORE FTIR GAS DETECTION SYSTEM

RELATED APPLICATIONS

The present application is a continuation of co-pending U.S. patent application Ser. No. 14/327,263 filed on Jul. 9, 2014 which claims the benefit under 35 U.S.C. §119(e) of U.S. Provisional Application Ser. No. 62/001,298, filed May 21, 2014, the contents of which are hereby incorporated by reference.

SUMMARY

Assorted embodiments configure a gas detection system to detect and measure amounts and types of gases flowing from a wellbore. A gas detection system can house a control module, infrared sensor, and first and second pumps in a portable case. The first and second pumps may be respectively positioned on opposite sides of the infrared sensor and configured to provide uniform sample gas flow through the infrared sensor to detect multiple different types of gasses flowing from the wellbore.

DETAILED DESCRIPTION

The present disclosure generally relates to a device capable of detecting the different mixed raw natural gasses using miniaturized Fourier Transform Infrared Spectroscopy (FTIR) sensor technology in the oil and gas field. More particularly in the detection of different raw natural gasses found in the drilling fluid during the exploration of oil and gas in a drilling process.

Advancements in oil exploration have allowed for faster and more efficient drilling operations. It can be advantageous to be able to detect the presence of hydrocarbons and the type of geological formations being penetrated during drilling operations. Analysis of drilling fluids that pass through an exploration bore can roughly measure hydrocarbon gases. Confirmed identification of hydrocarbons and other gases in drilling fluids can take time to analyze and may need precise conditions to accurately detect multiple different gases concurrently present flow from a wellbore. Such time expense and imprecision can correspond with drilling operations passing a geological formation, hydrocarbon reservoir, and zone of danger without detection. Hence, there is a continued goal to decrease the time needed to detect gasses in drilling fluids while increasing the accuracy and breadth of gases that can be detected.

Accordingly, a drilling fluid gas detection system may be connected to a wellbore and consist of a control module, infrared sensor, and first and second pumps in a portable case with the first and second pumps respectively positioned on opposite sides of the infrared sensor and configured to provide uniform sample gas flow through the infrared sensor to detect multiple different types of gasses flowing from the wellbore. The ability to provide uniform sample gas flow with dual pumps ensures that the infrared sensor is operating a maximum accuracy, which can correspond with increasingly accurate hydrocarbon detection and geological formation resolution. Control of the pumps can allow incorrect pressures and volumes of sample gas to flow through the FTIR assembly, be detected, and be cured by manipulating one pump in relation to the other to provide a corrected pressure and flow of sample gas.

Figure 1:
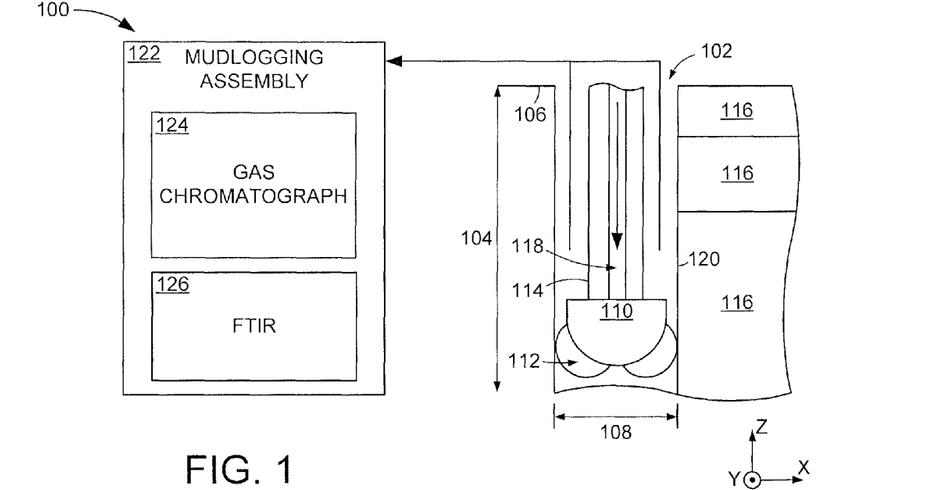
FIG. 1 displays a block representation of portions of an example drilling fluid gas detection environment utilized in accordance with various embodiments.

Although a drilling fluid gas detection system may be practiced in an unlimited variety of environments, such as a laboratory, FIG. 1 displays portions of an example drilling fluid gas detection environment 100 where various embodiments can be employed. The gas detection environment 100 has at least one exploration bore 102 that may extend a predetermined depth 104 from a ground surface 106 with at least a bore width 108. The bore width 108 may correspond with a drill bit 110 and an aggregate size of several drilling discs 112. The drill bit 110 can be forcibly rotated by a variety of means via one or more strings of drill pipe 114 configured for high torsion to allow the drill bit 110 to penetrate a number of different geological formations 116, such as sand, limestone, granite, as well as natural resource bearing rocks.

The rotation of the drill pipe 114 and drill bit 110 can create debris and heat. As strata of rock formations are punctured through drilling operations, natural gases found contained in the rock may be freed and can indicate the composition of rock, volume of hydrocarbons, and effectiveness of hydrocarbon extraction. Such freed natural gases are often pressed into and trapped within the drilling fluid, also known as "mud." The mud is pumped at high pressure back to the ground surface 106 via the central orifice 118 of the drill pipe 114 to cool and lubricate the drilling bit as it cuts through earth and rock. After passing through the drill bit 110, the mud can make its way back to the ground surface 106 between the drill pipe 114 and the bore sidewall 120.

The passage of drilling mud can entrap freed natural gases due at least to the density of the mud compared to the gases. The trapping of natural gases may further occur while the mud is under large pressures and as such the mud will be infused with the various gasses associated with the geological formations being fractured. That is, gasses emitted from oil and gas bearing rocks being drilled through are pressed into the mud via tremendous natural and artificial pressures associated with the drilling operations and the depth 104 of the drilling bore 102. With the various natural gasses entrapped into the mud, analysis of gasses within the mud returning to the surface can render the constituent gases and concentrations at various depths throughout the drilling bore 102.

While the drilling mud may be packaged and sent to a laboratory for analysis, such actions are not time efficient and can render geological formations and hydrocarbons undetected. Thus, a mudlogging assembly 122 can be configured to be located proximal the exploration bore 102 to allow for timely analysis of sample gasses that are previously extracted from the drilling fluids like mud. The mudlogging assembly 122 can have one or more different types of drilling fluid gas analyzing means, such as a mass spectrometer, gas chromatograph 124, and Fourier transform infrared spectroscopy (FTIR) assembly 126. It is contemplated that the gas chromatograph 124 may be utilized for some mudlogging conditions, such as high density drilling fluids, while the FTIR assembly 126 is utilized for other mudlogging conditions, such as when analysis time is critical, although it is contemplated that multiple different sensors and gas detection means can operate concurrently. The ability to selectively utilize the gas chromatograph 124 and FTIR assembly 126 to measure gases trapped in drilling fluids allows the mudlogging assembly 122 to adapt to changing drilling conditions and provide redundant detection of drilling fluid gases.

In some embodiments, the drilling fluid reaching the surface is immediately sent to a filter, such as a screen shaker, to remove the rock cuttings that can individually or collectively be analyzed for solid, liquid, and gas composition to indicate the type and formation of rock being drilled, which may provide verification of geologist's report and hydrocarbon reservoir estimations. While tools and instruments exist that are capable of measuring the extracted composition of gases that may emanate from the drilling bore 102, generally such equipment was not designed to operate concurrently on a single sample, survive the harsh operating environment of a drill site, be easily transported, or provide precise measurements in field conditions commonly found on a drill site.

For instance, a laboratory grade chromatograph, while a highly accurate tool in a laboratory setting, has not been adapted to the problematic electrical systems or harsh temperature and humidity often found in drilling environments. Such harsh environments will quickly degrade a typical laboratory grade chromatograph system into uselessness if employed proximal a wellbore. Also, such laboratory grade chromatograph equipment have not been readily reduced in size to allow for incorporation into physically robust casings, such as explosion-proof rated cases, at the drill site.

Further issues can plague field use of laboratory grade chromatograph systems as daily and sometimes hourly recalibrations are necessary to provide reliable measurements. The use of a chromatograph may include column chemicals that are hygroscopic, which poses a number of accuracy difficulties at a drill site as water is absorbed into the column chemicals making them useless over time for measuring well samples that often have both high levels of water vapor and oxygen. Laboratory grade chromatographs may also require a specific column temperature to be maintained within a very tight temperature range to garner repeatability and accuracy.

The various issues with measuring a gas sample using a chromatograph can be compounded by the lack of precision of the instrument, which is often is not reliable enough to discern different hydrocarbons, such as between Methane (C1) and Ethane (C2), as the Methane to Ethane ratio may be too large, such as a 90 to 1 ratio or more. Additionally, drilling fluid gasses can be so close in molecular weight that most if not all chromatographs have trouble returning to a baseline separation of these two gasses. Some chromatographs require large and heavy tanks of travel gas, such as Hydrogen or Helium. In the case of a flame ionization detector (FID) or other flame photometers, a special heavy and bulky FID fuel gas tank is utilized, which impedes the transport, set-up, and flexibility of the chromatograph as well as the administration of reliable tests. Further, the instrument becomes useless if any of these tank gasses run empty during operation.

Figure 2:
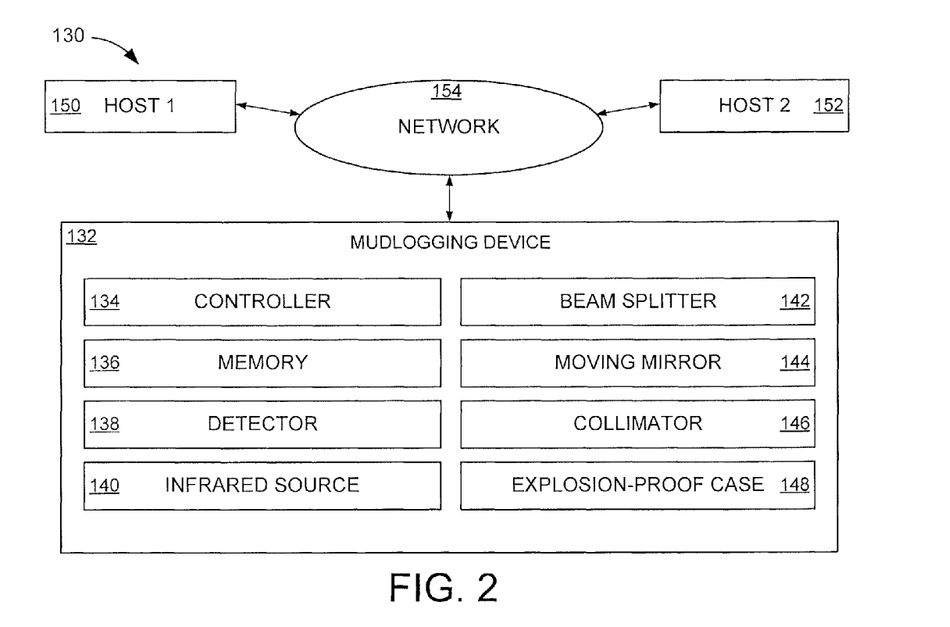
FIG. 2 illustrates a block representation of an example mudlogging assembly that may be utilized by the drilling fluid detection system of FIG. 1.

FIG. 2 is a block representation of an example mudlogging system 130 that may be incorporated into the mudlogging assembly 122 of FIG. 1 in accordance with some embodiments. At least one mudlogging device 132 can be employed by the mudlogging system 130 to extract sample gasses from drilling fluids, like drilling mud, and detect the type and quantity of the separated gasses present in the sample gas flow. Although not required or limiting, the mudlogging device 132 may have one or more local controllers 134, such as a microprocessor, that can access data present in rotating and solid-state memories 136 to execute software and analyze drilling fluid.

Subsequent to drilling fluid flowing through at least one extractor to separate gas and liquid constituent parts, sample gas from the drilling fluid may be analyzed by at least one detector 138 that measures the spectrum of light emitted as a result of passing an infrared light through sample gas. An infrared source 140 may be utilized in combination with a beam splitter 142, moving mirror 144, and collimator 146 to provide a spectrum that is analyzed using a Fourier transform by the controller 134 to identify the presence and amount of various gasses in the drilling fluid. It is contemplated that in the past, drilling fluid analysis and detection of natural gasses with Fourier Transform Infrared (FTIR) assemblies was difficult due to systems being too large, bulky, complex, and sensitive for utilization at the drilling site. Yet, advancements in computing and miniaturizing FTIR components have allowed FTIR assemblies to have a smaller footprint. As such, the mudlogging device 132 can now be constructed within a reasonable size and weight, such as 60 pounds or less, to be housed within an explosion-proof case 148 that is portable and rugged enough to reliably and accurately function at a drilling site.

It is contemplated that the mudlogging device 132 can operate independently and collectively to test sample gasses that are extracted from drilling fluid upstream from the detector 138. Various embodiments configure the controller 134 to establish, maintain, and terminate wired and wireless connections with various remote nodes, such as first 150 and second 152 hosts, via a network 154. The ability to connect the mudlogging device 132 to remote hosts 150 and 152 allows for minimal controller 134 and memory 136 size and computing power as remote computing hosts can provide data storage and execution. In other words, the ability to selectively utilize the network 154 to access one or more remotes hosts 150 and 152 allows the mudlogging device 132 to be configured with relatively low amounts of computing power and storage, which corresponds with a smaller physical footprint.

Figure 3:
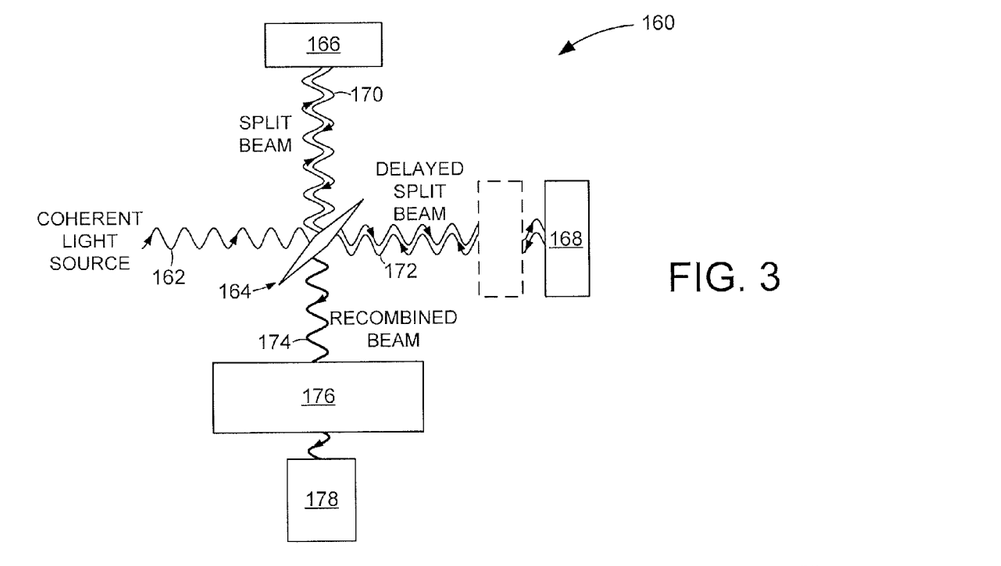
FIG. 3 is a diagram of an example Fourier transform infrared spectroscopy (FTIR) device that may be employed by the mudlogging assembly of FIG. 2.

FIG. 3 diagrams an overview of an example Fourier transform infrared spectroscopy (FTIR) device 160 that can be incorporated into a mudlogging device in accordance with assorted embodiments. As shown, the FTIR device 160 can have a coherent light source, such as the infrared source 150 of FIG. 2, which provides a source wave 162 at a predetermined frequency to a beam splitter 164. The beam splitter 164 can send 50% of the source wave 162 to a stationary mirror 166 and 50% of the source wave 162 to a moving mirror 168. The stationary mirror 166 can produce a split beam 170 while the moving mirror produces a delayed split beam 172 that are recombined by the beam splitter 164 into a sample beam 174 that passes through a sample 176. The difference in the split 170 and delayed split 172 beams allows wavelengths to be identified as different gases by the detector 178 in combination with Fourier transform analysis.

The FTIR device 160 can quickly provide accurate detection of diverse gases present in sample gas extracted from drilling fluids, the sample gas can be flowing at the time of detection. Such drilling fluid gas flow can provide efficient and accurate results when uniform gas flow and pressure is present at the FTIR, but non-uniform gas flow corresponding with varying sample gas volumes and pressures can degrade FTIR accuracy and speed. In order to provide efficient and accurate detection of constituent gasses in a gas sample, pressure and flow has to be regulated correctly to provide uniform gas flow. For example, too much pressure within the FTIR device 160 can present extra hydrocarbons and too little pressure within the FTIR device 160 can present too few hydrocarbons within a given sample.

Figure 4A:
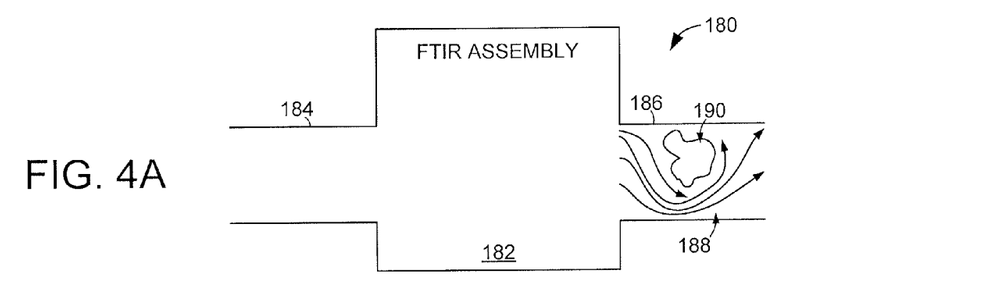
FIGS. 4A and 4B respectively show cross-section block representations of an example FTIR sensor that may be constructed and operated in accordance with various embodiments.
Figure 4B:
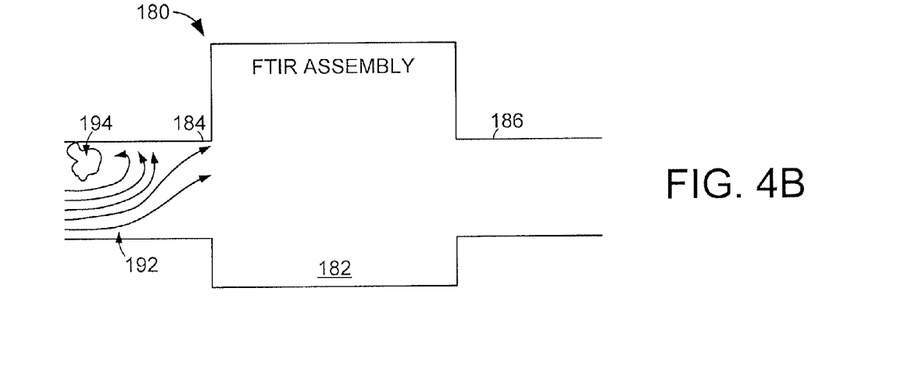

FIG. 4A and 4B respectively illustrate cross-section block representations of a portion of an example FTIR sensor 180 that can be experience uniform and non-uniform gas flow in various embodiments. The pressure and flow within the FTIR sensor 180 must be regulated in order to maintain accuracy. Within an explosion-proof housing or other type of housing, occlusions can and do occur due to any number of parameters, such as inlet fittings, exhaust fittings, line length, line size, presence of contaminants, and hydrocarbon drop out. In each drawing, the FTIR sensor 180 has an FTIR assembly 182 disposed between an inlet 184 and outlet 186. It is contemplated that the FTIR assembly 182 consists of a plurality of gas extraction and testing means, such as the various means shown in FIGS. 2-3, which allow constituent gasses of a sample to be identified.

In FIG. 4A, non-uniform sample gas flow 188 is shown by solid arrows. The presence of an occlusion 190 in the outlet 186 can temporarily and permanently produce the non-uniform flow that varies sample gas pressure in the FTIR assembly 182 and jeopardizes the accuracy of sample gas analysis. Because the exhaust occlusion 190 is variable for size, position, and interference, sample gas drawn from the FTIR assembly 182 into the outlet 186 will necessarily need a downstream exhaust pump to increase or decrease in speed in order to establish and maintain uniform sample gas flow and pressure through the FTIR assembly 182.

The uniform gas flow and pressure provides consistent sample gas volume in the FTIR assembly 182 and can correspond with fast, accurate, and reliable detection of gasses, particularly hydrocarbons. FIG. 4B also illustrates non-uniform sample gas flow 192, but originating from an occlusion 194 in the inlet 184 of the FTIR sensor 180. It is noted that an inlet 184 or outlet 186 occlusions can be any number, size, and type of foreign substances, such as solid and liquid debris as well as pockets of non-sample gasses, like air. Partial and complete occlusions may also occur simultaneously upstream and downstream from the FTIR sensor 180. It is further noted that an occlusion may occur for any length of time and may pass through the FTIR sensor 180 without any corrective actions being taken. However, because occlusion size and duration is variable, upstream inlet pumps can increase or decrease speed in order to regulate gas sample pressure and flow to provide uniform gas flow thought the FTIR assembly 182.

In some embodiments, non-uniform gas flows 188 and 192 may be individually and collectively characterized as turbulent sample gas flow. Such turbulent gas flow can occur with non-uniform gas volume or pressure passing into and out of the FTIR assembly 182. It can be appreciated that with the passage of infrared wavelengths through a sample to detect gasses, inconsistent sample gas pressure and volume can result in incorrect gasses being identified, incorrect amounts of gasses being detected, and gasses present in the sample being missed. Thus, the ability to detect turbulent flow in any part of the FTIR sensor 180 can allow upstream and downstream pumps, or compressors, to adjust to remove any occlusions and establish uniform sample gas flow through the FTIR assembly 182.

Figure 5:
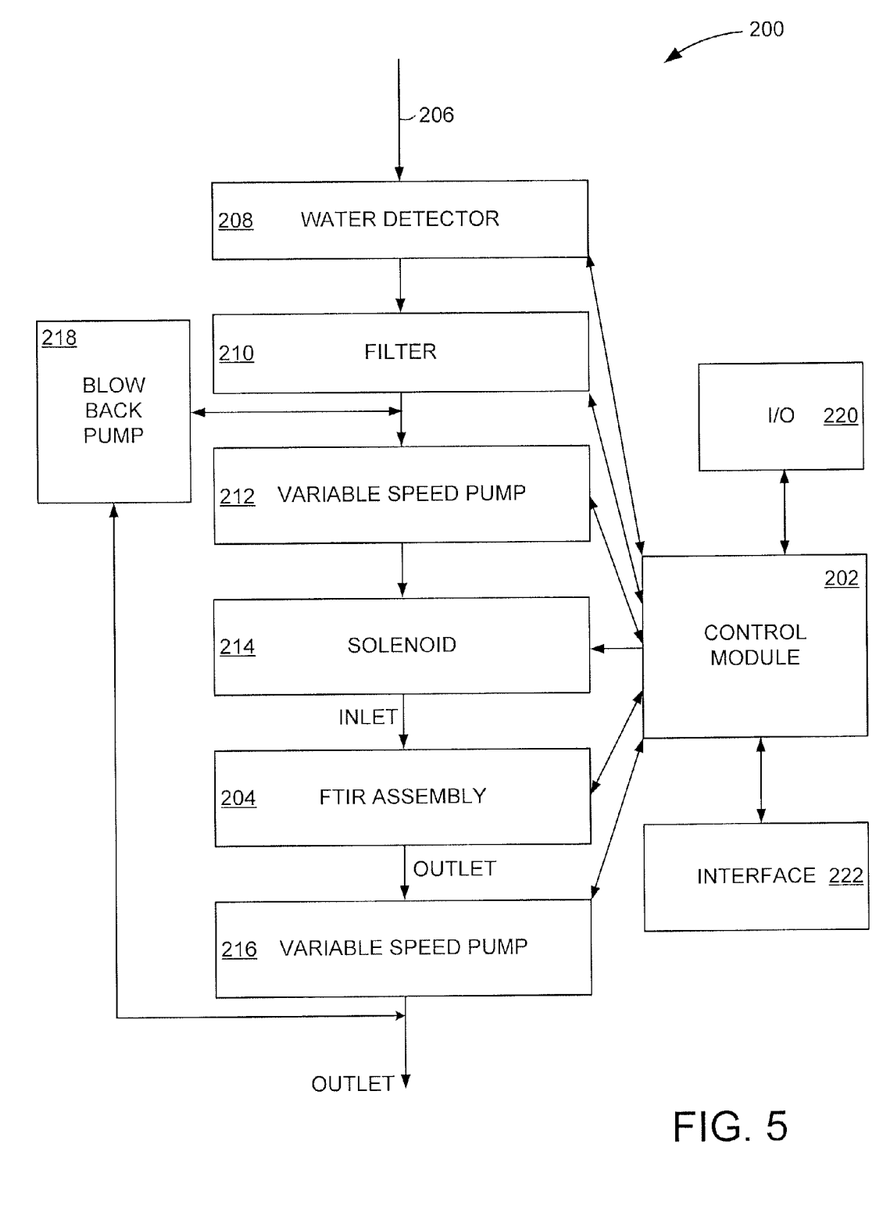
FIG. 5 conveys a perspective view of a portion of an example FTIR gas detection system configured in accordance with some embodiments.

FIG. 5 displays a block representation of an example FTIR gas detection system 200 that can be constructed and operated in accordance with assorted embodiments. It is to be understood that various embodiments may generally be directed to a mud gas detecting system capable of utilizing miniaturized FTIR detection components. It is a non-limiting purpose of the drilling fluid gas detection system 200 to provide uniform sample gas flow by using a tuned control module 202 to control the flow rate into and out of an FTIR assembly 204, automatically detect a partial or full occlusion in an inlet or outlet, and clear any occlusions that occur. It is contemplated that diverse, harsh, and variable environmental and operational conditions, such as ambient temperature, barometric pressure, humidity, and changes in drilling fluid characteristics, can be efficiently handled by the control module 202.

As discussed above, Fourier Transform Infrared Spectroscopy is a technique which can be utilized to obtain an infrared spectrum of absorption, emission, and photoconductivity, also known as Raman scattering of a solid, liquid, and gas. An FTIR spectrometer can be utilized to simultaneously collect spectral data in a wide spectral range that confers a significant advantage over a dispersive spectrometer which measures intensity over a narrow range of wavelengths at a time. The term Fourier Transform Infrared Spectroscopy originates from the fact that the mathematical Fourier transform process converts the raw data into the actual spectrum.

However, due to complexities the FTIR assembly 204 and the occurrence of variable gas pressures and flow within the FTIR assembly 204, which may correspond with one or more occlusions, efficient drilling fluid gas detection has yet to be optimized unless there is certain regulation of the pressure and flow of the sample gas. In the non-limiting example of FIG. 5, gasses can be quickly and accurately detected in a single continuous sample gas stream using the FTIR assembly 204 in combination with the control module 202 that is tuned to establish and maintain uniform drilling fluid gas flow and pressure through the FTIR assembly 204. The system 200 has an inlet 206 to let extracted drilling fluid gas pass through a water or contaminant detector 208. The water detector 208, which can also detect non-water contaminates, may be one or more electronic and mechanical sensors that can sense the presence of water and/or contaminates within the sample gas.

One or more filters 210 can subsequently eliminate particulates of various predetermined sizes, such as 1 µm. At least one variable speed pump 212 may be controlled by the control module 202 to provide uniform gas flow and pressure through a normally open solenoid 214 and to the inlet of the FTIR assembly. Upon detection of water or other liquid contaminate with the water detector 208, or in the event of a partial or full FTIR assembly inlet occlusion, the control module 202 can activate the solenoid 214, deactivate the inlet variable speed pump 212, deactivate the outlet variable speed pump 216, and then activate the blow back pump 218 in order to draw exhaust gasses and push any contaminates out of the inlet line 206, thereby clearing the occlusion. Further, a partial or full occlusion of the exhaust outlet can trigger the control module 202 to activate the inlet 212 and outlet 216 variable speed pumps to full power, thereby pushing the occlusion out of the exhaust outlet.

During operations in accordance with some embodiments, the control module 202 adjusts the respective speeds of the upstream and downstream variable speed pumps 212 and 216 to modulate the gas pressure and flow inside the FTIR assembly 204 and provide the uniform gas flow that corresponds with consistent sample gas pressure and volume the FTIR needs for optimized accuracy. It is noted that the pressures inside the FTIR assembly 204 dictate how much sample gas is being examined at any given time. Hence, occlusions and non-uniform flow at the FTIR assembly 204 can produce atmospheric pressure differences between the inlet and outlet of the FTIR assembly 204. In response to such change of sample gas flow, the control module 202 can independently and collectively increase and decrease the speed of the variable speed pumps 212 and 216 to overcome the occlusion and establish, or re-establish, correct, predetermined, uniform sample gas flow and pressure.

For example, if both pumps were set to 50% power, uniform gas flow and pressure through the FTIR assembly 204 could be attained. If a partial inlet occlusion is present, the control module 202 can increase the power to the upstream variable speed pump 212 to overcome the partial occlusion to re-establish an optimized atmospheric pressure inside the FTIR assembly 204. In various embodiments, as explained, upon detection of a full inlet occlusion in the FTIR assembly 204, the control module 202 can activate the blow back pump 218 to allow exhaust gas to be pushed back into the inlet and clear the occlusion.

As shown, the control module 202 can communicate with any component of the gas detection system 200. Such communication can allow for the continuous, sporadic, and routine monitoring of component status, pressures, adjustment, and gas flow as gasses are detected by the FTIR assembly 204. The control module 202 may pass any and all information collected from the system 200 to an external host via one or more input/output (I/O) modules 220. The I/O module 220 may be responsible for transmitting and receiving information to the outside world through wired and wireless networks accessed via appropriate protocol, such as encrypted protocol.

The gas detection system 200 may further have one or more interfaces 222 that communicate with a user and peripheral devices while enabling a network protocol to establish, maintain, and service the transfer of data across a network. The gas detection device components are not required or limiting, but can allow for data to be remotely computed via at least one processor, stored in a remote memory, and combined with data from other devices, such as other environmental, mechanical, and hydrocarbon detection equipment.

Figure 6:
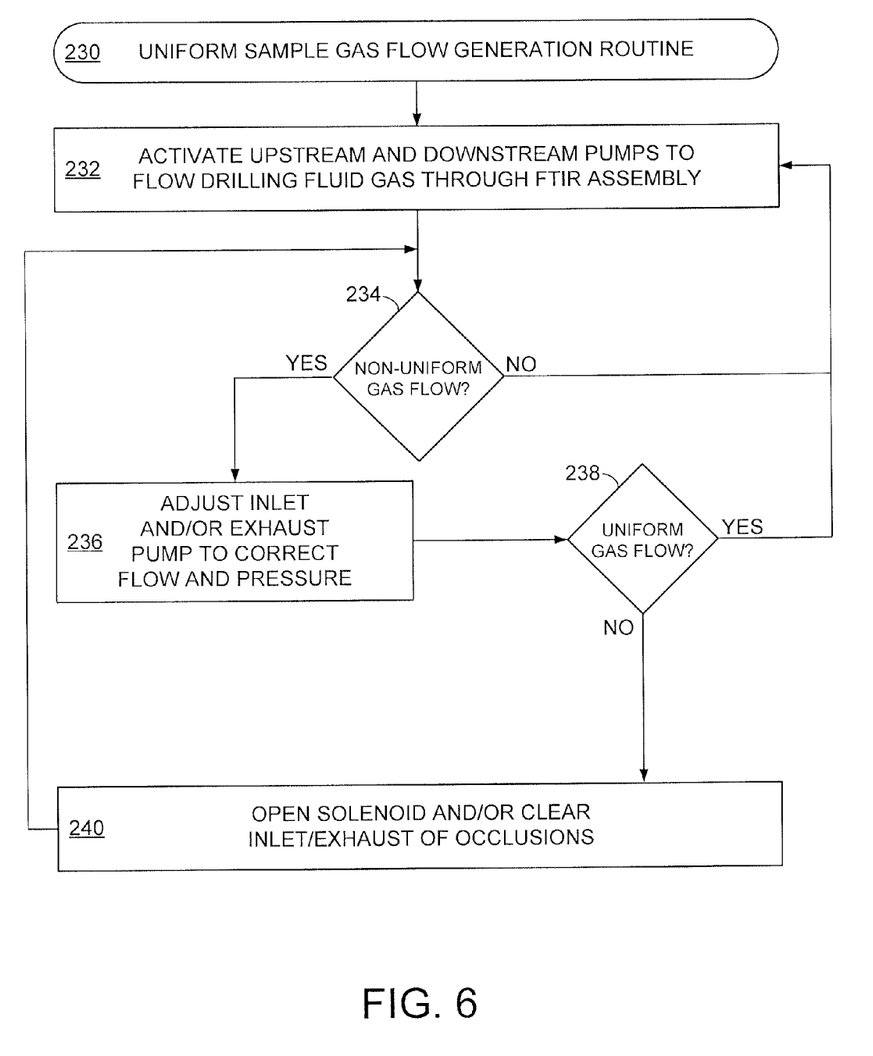
FIG. 6 is an example uniform sample gas flow routine that may be conducted in accordance with assorted embodiments.

FIG. 6 depicts an example uniform sample gas flow generation routine 230 that may be conducted at any time by a drilling fluid FTIR gas detection system in accordance with various embodiments. The routine 230 can begin with step 232 activating at least one upstream and downstream pump to flow sample gas extracted from drilling fluid through the FTIR assembly.

It is contemplated that step 232 can be conducted continuously, sporadically, and randomly without any other steps and decisions of routine 230 being conducted. However, various embodiments monitor one or both of the inlet and outlet of the FTIR assembly to detect if uniform gas pressure and/or volume are present in decision 234. If no non-uniform gas flow is detected in or around the FTIR assembly in decision 234, step 232 is revisited and conducted at will.

In the event decision 234 finds non-uniform flow, step 236 can re-regulate the upstream and downstream pumps, individually and concurrently, to bring the pressure and flow back into a uniform condition through the FTIR assembly. Step 236 may further involve altering the speed of the downstream pump in an attempt to overcome the exhaust occlusion causing the detected non-uniform flow. Step 236 may further involve altering the speed of the upstream pump in an attempt to overcome the inlet occlusion causing the detected non-uniform flow.

Upon further detection of a non-uniform flow in step 238, which may happen after failing to adjust either the upstream and/or downstream pumps in step 236 to overcome the non-uniform condition, various embodiments proceed to step 240. Although not limiting, step 240 can open one or more solenoids and pumps to bring exhaust gas upstream, such as to a position upstream of the closed solenoid or to the inlet of the upstream pump, which allows the blow back pump to push the exhaust gas into the inlet of the FTIR assembly and dislodge an inlet occlusion. Regardless of the actions taken in step 236, routine 230 can proceed to decision 238 where sample gas flow characteristics in and around the FTIR assembly are evaluated. If uniform flow is present, the actions of step 236 are logged as successful and step 232 returns to normal system operation.

A finding of continued non-uniform flow in decision 238 corresponds with step 236 failing and additional steps being taken to overcome any occlusions to the FTIR assembly. It is noted that the system can be completely taken offline with the FTIR assembly being deactivated or additional actions can be taken while FTIR readings are flagged as potentially inaccurate. In the event the FTIR assembly is active or not, step 240 can open the upstream solenoid and reverse gas flow through the FTIR assembly, which may be conducted in combination with the blow back pump. By reversing gas flow through the FTIR assembly, in accordance with some embodiments, a partial or full inlet occlusion can be overcome, but commonly at the cost of taking the gas detection system offline to allow for the reverse gas flow of step 242.

While the occlusion correction actions of steps 236 and 242 can efficiently overcome many occlusions, it is noted that further steps, such as mechanical cleaning of portions of the system may be in order to provide uniform gas flow. As such, the steps and decisions of routine 230 are not required or limiting and various actions can be added and removed to establish and maintain uniform gas flow through the FTIR and accurate detection of gasses contained in the sample gas, as extracted from drilling fluid. For example, an additional step may be to notify a remote host, such as a site manager, that an occlusion has occurred so that the upstream gas extractor can be checked to ensure proper separation of drilling fluids from gasses contained therein.

In various embodiments, routine 230 involves the logging of occlusion events in relation to a variety of parameters, such as air temperature, drilling fluid density, drill bore depth, rock formation being punctured, humidity, and status of an upstream filter. Such occlusion event tracking can allow for one or more local and remote controllers and hosts to predict a likelihood of an occlusion occurring. For example, drilling through limestone beyond 1,000 feet with drilling mud having a particular range of density can be identified as in high risk of occluding the FTIR assembly. In response to the predictions, the gas detection system can adapt to the drilling fluid parameters to reduce the risk of occlusions, such as by activating additional gas separation and filtering means, which may take into account past corrective actions executed to overcome occlusions with similar drilling fluid parameters.

Through the tuned configuration of an FTIR gas detection system with multiple variable speed pumps on opposite sides of an FTIR assembly, occlusions and non-uniform pressures and flow to the FTIR assembly can be efficiently overcome to establish and maintain uniform sample gas pressures and flow. The detection of inaccurate FTIR sample gas pressures and flow along with the variety of corrective actions that may be conducted by having upstream and downstream pumps can allow the FTIR assembly to continuously operate as variations in sample gas flow are quickly identified and corrected by tuned control of the system pumps. Moreover, the ability to predict high risk potential for FTIR assembly occlusions can allow the system to take proactive measures to maintain uniform sample gas flow and pressure to minimize the number and severity of occlusions.

What is claimed is:

1. An apparatus comprising a mudlogging assembly connected to a wellbore, the mudlogging assembly comprising a Fourier Transform Infrared (FTIR) detector and a second infrared detector gas analyzing means each positioned between first and second pumps inside a portable housing, the mudlogging assembly configured to measure raw natural gasses extracted from a drilling fluid obtained from the wellbore.

2. The apparatus of claim 1, wherein the portable housing is an explosion-proof case.

3. The apparatus of claim 1, wherein the portable housing weighs 60 pounds or less.

4. The apparatus of claim 1, wherein the portable housing is positioned on a drilling site.

5. The apparatus of claim 1, wherein a water detector is positioned upstream of the first pump inside the portable housing.

6. The apparatus of claim 1, wherein at least one filter is positioned upstream of the first pump inside the portable housing.

7. The apparatus of claim 6, wherein the FTIR detector comprises stationary and moving mirrors.

8. The apparatus of claim 6, wherein the at least one filter is configured to catch contaminates of 1 µm or larger in size.

9. The apparatus of claim 6, wherein two different types of particulate filters are present in the portable housing.

10. The apparatus of claim 1, wherein a control module is positioned in the portable housing and connected to each gas analyzing means and each pump.

11. The apparatus of claim 10, wherein the portable housing comprises a communication interface connecting the control module to a remote network host.

12. A method comprising;
arranging a mudlogging assembly in a portable housing, the mudlogging assembly comprising a Fourier Transform Infrared (FTIR) detector and a gas chromatograph gas analyzing means each positioned between first and second pumps inside the portable housing;
connecting the mudlogging assembly to a wellbore to detect extracted gasses from a drilling fluid obtained from the wellbore; and
analyzing the drilling fluid with each gas analyzing means to provide redundant detection of two or more hydrocarbons entrapped in the drilling fluid.

13. The method of claim 12, wherein a mass spectrometer gas analyzing means is positioned between the first and second pumps in the portable housing.

14. The method of claim 13, wherein at least two gas analyzing means operate concurrently.

15. The method of claim 13, wherein each gas analyzing means operates independently and successively.

16. The method of claim 12, wherein the analyzing step differentiates between Methane and Ethane hydrocarbons entrapped in the drilling fluid.

17. A method comprising:
arranging a mudlogging assembly in a portable housing, the mudlogging assembly comprising a Fourier Transform Infrared (FTIR) detector and a gas chromatograph gas analyzing means each positioned between first and second pumps inside the portable housing;
connecting the mudlogging assembly connected to a wellbore;
detecting an occlusion in the mudlogging assembly and analyzing a drilling fluid with at least a gas analyzing means to provide redundant detection of two or more hydrocarbons entrapped in the drilling fluid.

18. The method of claim 17, wherein the first and second pumps are each variable speed pumps.

19. The method of claim 17, wherein the first and second pumps are directed by a controller of the mudlogging assembly to maintain a uniform pressure through the mudlogging assembly.

20. The method of claim 17, wherein the mudlogging assembly comprises a local memory positioned in the portable housing and configured to log the detection of the two or more hydrocarbons.

* * * * *